(12) United States Patent
Hashimoto et al.

(10) Patent No.: US 11,648,340 B2
(45) Date of Patent: May 16, 2023

(54) EXTRACORPOREAL CIRCULATION APPARATUS

(71) Applicant: TERUMO KABUSHIKI KAISHA, Tokyo (JP)

(72) Inventors: Tomoaki Hashimoto, Kanagawa (JP); Tsuyoshi Hasegawa, Kanagawa (JP); Ryohei Katsuki, Kanagawa (JP); Yuuki Hara, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 770 days.

(21) Appl. No.: 16/531,374

(22) Filed: Aug. 5, 2019

(65) Prior Publication Data
US 2019/0351128 A1 Nov. 21, 2019

Related U.S. Application Data

(63) Continuation of application No. PCT/JP2018/004858, filed on Feb. 13, 2018.

(30) Foreign Application Priority Data

Feb. 22, 2017 (JP) .............................. JP2017-030797

(51) Int. Cl.
 *A61M 1/36* (2006.01)
 *G01F 23/292* (2006.01)
(52) U.S. Cl.
 CPC ......... *A61M 1/3624* (2013.01); *G01F 23/292* (2013.01); *A61M 2205/3334* (2013.01); *A61M 2205/3379* (2013.01)

(58) Field of Classification Search
 CPC .............. A61M 1/3221; A61M 1/3624; A61M 1/3626; A61M 1/3627; A61M 2205/3334; A61M 2205/3379; G01F 23/292
 See application file for complete search history.

(56) References Cited

U.S. PATENT DOCUMENTS

2010/0086172 A1* 4/2010 Venkoparao .......... G01F 23/802
 382/173
2016/0375185 A1* 12/2016 Meisberger ......... A61M 1/0259
 250/341.7
(Continued)

FOREIGN PATENT DOCUMENTS

EP 0952433 B1 2/2008
JP H07120292 A 5/1995
(Continued)

OTHER PUBLICATIONS

Written Opinion of the International Searching Authority, PCT/JP2018/004858, dated Feb. 13, 2018, Terumo Kabushiki Kaisha, dated Apr. 17, 2018.

(Continued)

*Primary Examiner* — Philip R Wiest
(74) *Attorney, Agent, or Firm* — MacMillan, Sobanski & Todd, LLC

(57) ABSTRACT

An extracorporeal circulation apparatus has a blood reservoir temporarily storing blood and a presence information acquisition unit to detect presence or absence of blood at respective wall locations in a two-dimensional array. A control unit determines the position of a blood surface on the basis of consecutive elements in the array having detected blood along at least one of a first direction parallel to the blood surface and a second direction perpendicular to the blood surface.

6 Claims, 8 Drawing Sheets

(56) References Cited

U.S. PATENT DOCUMENTS

2019/0070353 A1* 3/2019 Knott .................. A61M 1/3621
2019/0351128 A1* 11/2019 Hashimoto ............. G01F 23/02

FOREIGN PATENT DOCUMENTS

JP          2006138814 A    6/2006
JP          2010207349 A    9/2010

OTHER PUBLICATIONS

International Search Report, PCT/JP2018/004858, Apr. 4, 2018.
Extended European Search Report, EP18756770.6, dated Nov. 17, 2020.

* cited by examiner

EXTRACORPOREAL CIRCULATION APPARATUS

CROSS REFERENCE TO RELATED APPLICATIONS

This application is a continuation of PCT Application No. PCT/JP2018/004858, filed Feb. 13, 2018, based on and claiming priority to Japanese Application No. 2017-030797, filed Feb. 22, 2017, both of which are incorporated herein by reference in their entirety.

BACKGROUND OF THE INVENTION

The present invention relates to an extracorporeal circulation apparatus that subjects blood to extracorporeal circulation.

When cardiac surgery for a patient is conducted, for example, an extracorporeal circulation apparatus is used. In the extracorporeal circulation apparatus, extracorporeal blood circulation in which a pump operates to remove blood from the patient via a tube, gas exchange in the blood and body temperature adjustment are performed by an oxygenator, and the blood is thereafter again returned to the patient via the tube, auxiliary circulation, and the like are performed. In such extracorporeal blood circulation and the like, the blood removed from the patient and the blood bled during surgery are temporarily stored and managed in a blood reservoir, before being guided to the oxygenator. This enables the blood to smoothly flow in a circulation circuit.

The amount of blood that is stored in the blood reservoir exerts an influence on a state of the patient. Accordingly, it is demanded to safely and reliably manage the amount of the blood (position of the blood surface) to be stored in the blood reservoir. As a detection method of a liquid surface, proposed are a detection method using an electrostatic capacitance scheme in which a liquid surface is detected on the basis of a change in an electrostatic capacitance that is generated between two electrodes, a detection method of an ultrasound scheme in which a liquid surface is detected on the basis of the time from when ultrasound is issued to when the ultrasound is returned after being reflected on the liquid, and the like. However, the liquid surface detection methods of the electrostatic capacitance scheme and the ultrasound scheme can detect whether the liquid surface is lower than a prescribed liquid surface position, but cannot detect a continuous change in the liquid surface in some cases. Moreover, a liquid surface being lower than a prescribed liquid surface position cannot be reliably detected in some cases, due to the shape of a container, such as a blood reservoir, in which the liquid is stored, and a surrounding environment.

Japanese patent publication JPH07-120292 discloses a liquid surface detection apparatus provided with an imaging device that captures an image of a sample solution in order to position a suction nozzle relative to a surface of the sample solution. In the liquid surface detection apparatus described in JPH07-120292, light emitted from a light source is transmitted through a container including the sample solution. The light transmitted through the container including the sample solution is converted into an electric signal by the imaging device. The intensity of the light converted into the electric signal is binarized according to a threshold (i.e., a binary image is created by replacing all pixel values above the threshold with a value of 1 and replacing all other pixels with a value of 0). The liquid surface detection apparatus described in JPH07-120292 measures a position where a liquid surface is present on the basis of binarized data.

However, blood has comparatively high viscosity, and thus is easy to adhere on an inner wall of a blood reservoir. Accordingly, even when the position of the surface of the blood stored in the blood reservoir is lowered, the blood in the blood reservoir sticks and remains on the inner wall of the blood reservoir at positions above the actual blood surface in some cases. Accordingly, sole reliance on imaging light that has been transmitted through the container including a liquid by the imaging device causes a noise to be generated by the blood having adhered on the inner wall of the blood reservoir, and there is a concern that the position of a liquid surface (blood surface) of the blood stored in the blood reservoir cannot be reliably detected.

SUMMARY OF THE INVENTION

The present invention has been made in order to solve the problem, and aims to provide an extracorporeal circulation apparatus capable of reliably detecting the position of a liquid surface (blood surface) stored in a blood reservoir.

According to the present invention, the abovementioned problem is solved by an extracorporeal circulation apparatus configured to subject blood to extracorporeal circulation, the extracorporeal circulation apparatus including: a blood reservoir configured to store the blood temporarily; a presence information acquisition unit configured to acquire blood detection values spanning a two-dimensional array mapped to a predetermined wall of the reservoir, each blood detection value for a respective element of the array being indicative of whether blood stored in the blood reservoir is present at the respective wall location. A control unit is programmed to determine a position of a surface of the stored blood on the basis of finding a predetermined number of consecutive elements having a blood detection value indicating a presence of stored blood along at least one of a first direction parallel to the surface of the blood stored in the blood reservoir and a second direction perpendicular to the surface of the blood.

With the abovementioned configuration, the control unit executes control to determine the position of the blood surface on the basis of presence or absence of consecutiveness between pieces of the presence information acquired along at least one of the first direction parallel to the blood surface of the blood stored in the blood reservoir and the second direction perpendicular to the blood surface among pieces of the presence information transmitted from the presence information acquisition unit that acquires the presence information on the blood stored in the blood reservoir. In other words, the control unit identifies the position of the liquid surface (blood surface) of the blood stored in the blood reservoir on the basis of wall locations which are at a center of groups of consecutive wall locations for which the presence of blood is detected. Accordingly, the control unit can remove a noise that is generated by the blood adhered on the inner wall of the blood reservoir. This enables the extracorporeal circulation apparatus of the present invention to reliably detect a position of the liquid surface (blood surface) of the blood stored in the blood reservoir.

Moreover, generally, a filter member for removing bubbles and foreign matters in the blood flowing into an inside of the blood reservoir is disposed inside the blood reservoir. Because the filter member has comparatively fine meshes, depending on the amount of blood flowing into the inside of the blood reservoir, the amount of blood passing thorough the filter member may be less than the amount of blood flowing into the blood reservoir in some cases. This may cause the blood surface inside the filter member to be higher than the blood surface (blood surface that is intended to be originally detected) in the blood reservoir in some cases. Accordingly, a noise due to the filter member may be generated in some cases. In contrast, with the abovementioned configuration, the control unit can determine whether there is consecutiveness between pieces of the presence information acquired along both of the first direction parallel to the blood surface and the second direction perpendicular to the blood surface, and can determine the position of the liquid surface (blood surface) of the blood stored in the blood reservoir on the basis of the determination result. This enables the extracorporeal circulation apparatus of the present invention to detect the position of the blood surface that rises in the filter member and to remove a noise (noise due to the filter member) from the blood surface that rises in the filter member, and thus to reliably detect the position of the liquid surface (blood surface) of the blood stored in the blood reservoir.

Preferably, the presence information acquisition unit is an imaging unit that is disposed outside the blood reservoir and images the blood surface.

With the abovementioned configuration, the imaging unit, serving as the presence information acquisition unit, is disposed outside the blood reservoir and images the blood surface. Accordingly, the imaging unit images the blood surface in a noncontact state to the blood, and acquires pieces of presence information on the blood stored in the blood reservoir. This enables the extracorporeal circulation apparatus of the present invention to detect a continuous change in the blood surface, unlike the liquid surface detection methods of the electrostatic capacitance scheme and of the ultrasound scheme.

Preferably, the presence information is color information, and the control unit executes a binarization process on the basis of the color information transmitted from the presence information acquisition unit, and executes the control to determine the position of the blood surface.

With the abovementioned configuration, the presence information on the blood is color information. The blood contains a component of red. Therefore, the control unit executes a binarization process on the basis of the color information transmitted from the presence information acquisition unit, extracts the blood containing the component of red, and determines the position of the blood surface. This enables the control unit to more rapidly and reliably determine the position of the blood surface.

Alternatively, the presence information acquisition unit is a temperature detection unit that is attached to a wall surface of the blood reservoir, and detects the temperature of the wall surface along at least one of the first direction and the second direction.

With the abovementioned configuration, the temperature detection unit, serving as the presence information acquisition unit, is attached to the wall surface of the blood reservoir, and detects the temperature of the wall surface of the blood reservoir along at least one of the first direction and the second direction. The temperature of the blood removed from the patient and stored in the blood reservoir is higher than the temperature of the air. Accordingly, the temperature of the wall surface of a blood-holding portion of the blood reservoir is higher than the temperature of the wall surface of a no blood-holding portion of the blood reservoir (portion of the air). The temperature detection unit detects such a difference and a change in the temperature between the wall surfaces of the blood reservoir, and acquires pieces of presence information on the blood stored in the blood reservoir. This enables the extracorporeal circulation apparatus of the present invention to detect a continuous change in the blood surface, unlike the liquid surface detection methods of the electrostatic capacitance scheme and of the ultrasound scheme.

Alternatively, the presence information acquisition unit is a thermography unit that is disposed outside the blood reservoir and detects infrared rays to be emitted from the blood reservoir in which the blood has been stored.

With the abovementioned configuration, the thermography unit, serving as the presence information acquisition unit, is disposed outside the blood reservoir, and detects infrared rays emitted from the blood reservoir in which the blood has been stored. The temperature of the blood removed from the patient and stored in the blood reservoir is higher than the temperature of the air. Accordingly, the temperature of a blood-holding portion of the blood reservoir is higher than the temperature of a no blood-holding portion of the blood reservoir (portion of the air). The thermography detects such a difference and a change in the temperature of the blood reservoir as a difference and a change in the amount of radiation of infrared rays, and acquires pieces of presence information on the blood stored in the blood reservoir. This enables the extracorporeal circulation apparatus of the present invention to detect a continuous change in the blood surface, unlike the liquid surface detection methods of the electrostatic capacitance scheme and of the ultrasound scheme.

Preferably, the presence information is temperature information, and the control unit executes a binarization process on the basis of the temperature information transmitted from the presence information acquisition unit, and executes the control to determine the position of the blood surface.

With the abovementioned configuration, the presence information on the blood is temperature information. The amount of infrared rays emitted from a measurement object depends on the temperature of the measurement object. Accordingly, the presence information (the amount of emitted infrared rays) transmitted from the thermography unit is equivalent to the temperature information. The control unit executes a binarization process on the basis of the temperature information transmitted from the presence information acquisition unit, and extracts a portion in which the blood has been stored in the blood reservoir to determine the position of the blood surface. This enables the control unit to rapidly and reliably determine the position of the blood surface.

The extracorporeal circulation apparatus preferably further includes a display unit that displays information on the position of the blood surface determined by the control unit, wherein the information is transmitted from the control unit.

With the abovementioned configuration, the display unit displays information on the position of the blood surface determined by the control unit. Accordingly, a health care worker can more easily manage the position of the blood surface in the blood reservoir by checking the display unit. This enables the extracorporeal circulation apparatus of the present invention to attain the enhancement of support with respect to a procedure by the health care worker.

Preferably, the control unit includes a storage unit that stores therein information on the position of the blood surface, and executes, when a change value between the information on the position of the blood surface stored in the storage unit and the determined information on the position of the blood surface is greater than a predetermined change value, control to make a notification about a change tendency.

With the abovementioned configuration, the control unit executes, when a change value between the information on the position of the blood surface stored in the storage unit and the determined information on the position of the blood surface is greater than a predetermined change value, control to make a notification about a change tendency. Accordingly, before the position of the blood surface in the blood reservoir is lowered than a predetermined position, for example, a warning position, or before approaches the predetermined position, the control unit can notify a health care worker of the change value of the blood surface being greater than the predetermined change value. This enables the extracorporeal circulation apparatus of the present invention to attain the enhancement of support with respect to a procedure by the health care worker.

Preferably, the apparatus includes a circulation circuit that causes the blood to circulate; a pump that is disposed in the circulation circuit, and sends out the blood from an inside of the circulation circuit; and a motor that rotates on the basis of a signal transmitted from the control unit, and drives the pump. When the determined position of the blood surface is higher than a reference position, the control unit raises a rotational speed of the motor, and when the determined position of the blood surface is lower than the reference position the control unit lowers the rotational speed of the motor.

With the abovementioned configuration, the control unit executes control to raise the rotational speed of the motor when the determined position of the blood surface is higher than the reference position. This raises the rotational speed of the pump, and increases the amount of blood to be sent out by the pump. Accordingly, the amount of blood to be sent from the blood reservoir to a patient increases, thereby decreasing the amount of blood in the blood reservoir. On the other hand, the control unit executes control to lower the rotational speed of the motor when the determined position of the blood surface is lower than the reference position. This lowers the rotational speed of the pump, and decreases the amount of blood to be sent out by the pump. Accordingly, the amount of blood to be sent from the blood reservoir to a patient decreases, thereby increasing the amount of blood in the blood reservoir. This maintains the position of the blood surface in the blood reservoir to a constant position. In other words, the extracorporeal circulation apparatus of the present invention can control the position of the blood surface in the blood reservoir to the constant position. This enables the extracorporeal circulation apparatus of the present invention to attain the enhancement of support with respect to a procedure by the health care worker.

With the present invention, it is possible to provide an extracorporeal circulation apparatus capable of reliably detecting the position of a liquid surface (blood surface) stored in a blood reservoir.

DETAILED DESCRIPTION OF PREFERRED EMBODIMENTS

Figure 1:
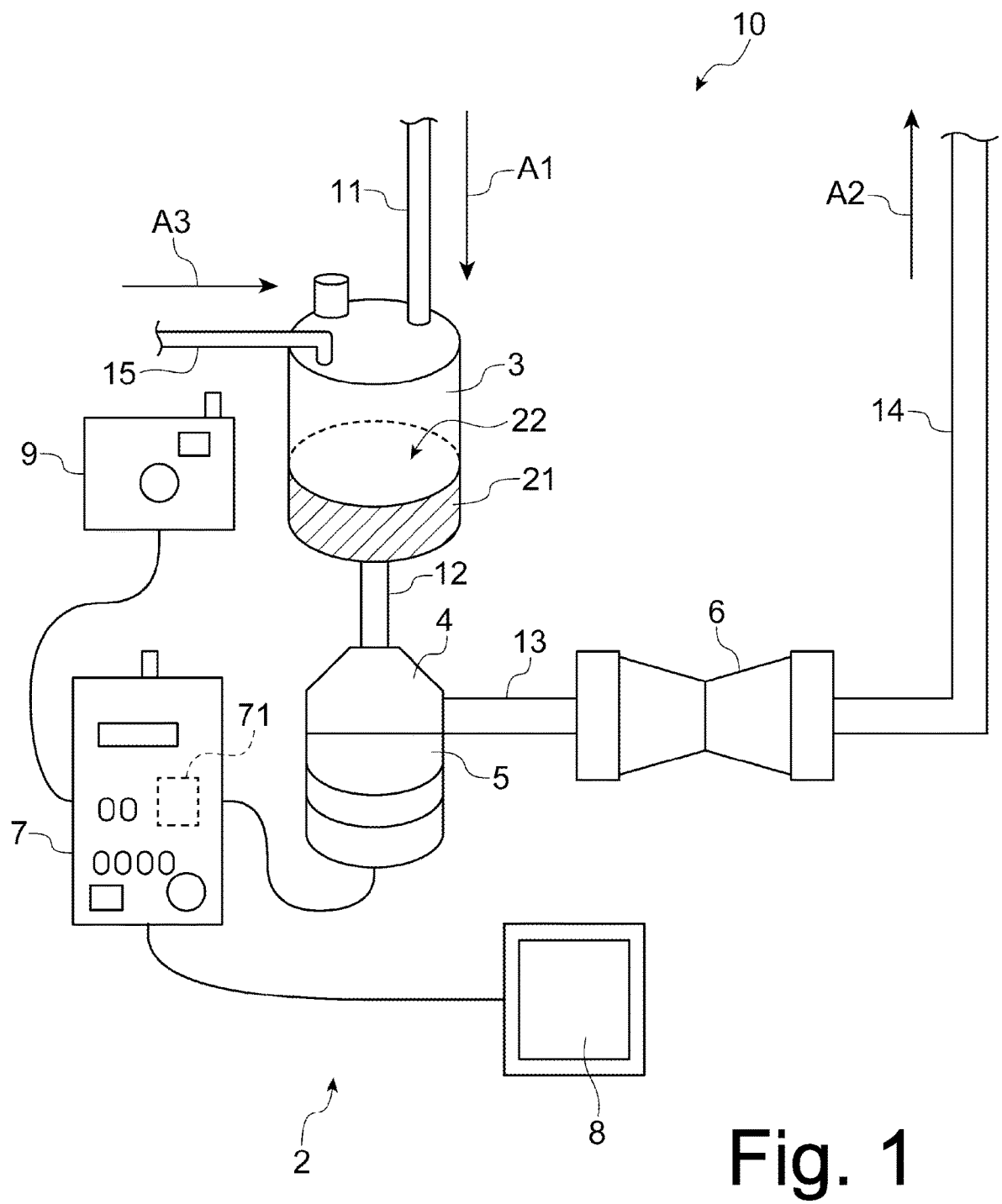
FIG. 1 is a system diagram illustrating an extracorporeal circulation apparatus according to a first embodiment of the present invention.

Preferred embodiments of the present invention will be described below in details with reference to the drawings. Note that, the embodiments of the present invention that will be described below are preferable specific examples, and technically preferable various limitations are thus set thereto; however, the scope of the present invention is not limited to these aspects unless otherwise specifically stated that the present invention is limited in the description below. Moreover, in the respective drawings, the similar components are assigned with the same reference numerals, and detailed explanations thereof are omitted as appropriate.

FIG. 1 is a system diagram illustrating an extracorporeal circulation apparatus according to a first embodiment of the present invention. The extracorporeal circulation apparatus 2 illustrated in FIG. 1 can conduct an "extracorporeal circulation operation".

The "extracorporeal circulation operation" indicates, for example, in such a case that the blood circulation in the heart is temporarily stopped due to cardiac surgery, a circulation operation of blood and a gas exchange operation (oxygen addition and/or carbon dioxide removal) with respect to the blood are performed by the extracorporeal circulation apparatus 2.

For example, when cardiac surgery for a patient is performed, the extracorporeal circulation apparatus 2 illustrated in FIG. 1 can perform oxygenator extracorporeal blood circulation in which a pump 4 of the extracorporeal circulation apparatus 2 is operated to remove blood from the patient, the blood having been stored in a blood reservoir 3 is sent to an oxygenator 6, gas exchange in the blood is performed by the oxygenator 6 to subject the blood to oxygenation, and thereafter, the blood having been subjected to the oxygenation is again returned to the patient. The extracorporeal circulation apparatus 2 is an apparatus that acts as an alternative to the heart and the lungs.

As illustrated in FIG. 1, the extracorporeal circulation apparatus 2 according to the embodiment is provided with the blood reservoir 3, the pump 4, a motor 5, the oxygenator 6, a control unit 7, a display unit 8, an imaging unit ("presence information" acquisition unit) 9, and a circulation circuit 10.

The circulation circuit 10 includes an instrument (blood removal cannula or the like) for removing blood from the patient, which is not illustrated, a blood removal tube (also referred to as a blood removal line) 11, a first connection tube 12, a second connection tube 13, a blood transmission tube (also referred to as a blood transmission line) 14, an instrument (blood transmission cannula or the like) for transmitting blood to the patient, which is not illustrated, and a third connection tube 15, and is disposed as a circuit that subjects blood to extracorporeal circulation.

A tip of the blood removal cannula is inserted into a superior vena cava, an inferior vena cava, and the like of the patient, and is indwelled. The blood removal cannula is connected to the blood reservoir 3 via the blood removal tube 11. As an arrow A1 illustrated in FIG. 1, the blood removal tube 11 is a duct line that guides the blood removed from the patient with the blood removal cannula to the blood reservoir 3. The first connection tube 12 is connected to the blood reservoir 3 and the pump 4. In other words, one end portion of the first connection tube 12 is connected to the blood reservoir 3. The other end portion of the first connection tube 12 is connected to the pump 4. The first connection tube 12 is a duct line that guides the blood stored in the blood reservoir 3 to the pump 4. The second connection tube 13 is connected to the pump 4 and the oxygenator 6. In other words, one end portion of the second connection tube 13 is connected to the pump 4. The other end portion of the second connection tube 13 is connected to the oxygenator 6. The second connection tube 13 is a duct line that guides the blood sent out from the pump 4 to the oxygenator 6. As an arrow A2 illustrated in FIG. 1, the blood transmission tube 14 is a duct line that guides the blood passed through the oxygenator 6 to the blood transmission cannula. The blood transmission cannula is inserted from an aorta and the like, and is connected to the oxygenator 6 via the blood transmission tube 14. The blood transmission cannula causes the blood passed through the oxygenator 6 to return to the patient. As an arrow A3 illustrated in FIG. 1, the third connection tube 15 is a duct line that guides the blood bled during surgery to the blood reservoir 3.

As the blood removal tube 11, the first connection tube 12, the second connection tube 13, the blood transmission tube 14, and the third connection tube 15, for example, duct lines made of a synthetic resin having high transparency and elastically deformable flexibility, such as a vinyl chloride resin and a silicone rubber, are used.

The blood reservoir 3 is a container having a storage space (reservoir chamber) inside, and temporarily stores therein blood 21 that is blood removed from the patient via the blood removal cannula and the blood removal tube 11, and is blood bled during surgery and guided through the third connection tube 15. The blood reservoir 3 temporarily stores therein the blood 21 to allow the blood removed from the patient to smoothly flow neither more nor less in the circulation circuit 10.

Examples of materials for the blood reservoir 3 include polycarbonate, an acrylic resin, polyethylene terephthalate, polyethylene, polypropylene, polystyrene, polyvinyl chloride, an acrylic-styrene copolymer, and an acrylic-butadiene-styrene copolymer.

The pump 4 is disposed in the circulation circuit 10 between the blood reservoir 3 and the oxygenator 6, and operates by a driving force transmitted from the motor 5. In other words, the motor 5 is disposed as a driving device for driving the pump 4. The motor 5 rotates on the basis of a signal transmitted from the control unit 7, and drives the pump 4. The pump 4 operates by the driving force transmitted from the motor 5, and sends out the blood from the inside of the circulation circuit 10. Specifically, the pump 4 allows the blood 21 temporarily stored in the blood reservoir 3 to pass through the oxygenator 6, and thereafter to return to the patient via the blood transmission tube 14. As the pump 4, for example, a centrifugal pump or a roller pump is used.

The oxygenator 6 is disposed in the circulation circuit 10 downstream of the pump 4 in the example illustrated in FIG. 1, and performs a gas exchange operation (oxygen addition and/or carbon dioxide removal) with respect to the blood. Note that, a disposed position of the oxygenator 6 is not limited to the position exemplified in FIG. 1. The oxygenator 6 is, for example, a membrane oxygenator, and is specially preferably a hollow fiber membrane oxygenator. An oxygen gas is supplied to the oxygenator 6 from an oxygen gas supply unit, which is not illustrated.

The control unit 7 transmits a control signal with respect to the motor 5, and controls an operation of the motor 5. Moreover, the control unit 7 transmits an information signal to the display unit 8, and causes the display unit 8 to display information on a liquid surface (blood surface) 22 of the blood 21 stored in the blood reservoir 3 (e.g., the height of the blood surface or a corresponding volume of blood). Note that, a disposed position of the display unit 8 is not specially limited. For example, the display unit 8 may be integrally disposed with the control unit 7. In this case, the control unit 7 causes the display unit that is included in the control unit 7 to display information on the blood surface 22. Moreover, the control unit 7 determines the position of the blood surface 22 on the basis of a signal (presence information on the blood 21) transmitted from the imaging unit 9. This will be described in details later. In addition, the control unit 7 includes a storage unit 71, and can store information on the position of the blood surface 22 in the storage unit 71.

The display unit 8 displays, on the basis of the information signal transmitted from the control unit 7, the information on the position of the blood surface 22 of the blood 21 stored in the blood reservoir 3. As the display unit 8, for example, a liquid crystal display or an organic electroluminescence (EL) display is used.

The imaging unit 9 corresponds to the presence information acquisition unit of the present invention, acquires presence information on the blood 21 stored in the blood reservoir 3. Specifically, the imaging unit 9 is disposed outside the blood reservoir 3, and images the blood surface 22 of the blood 21 stored in the blood reservoir 3. The image imaged by the imaging unit 9 is transmitted to the control unit 7.

The amount of the blood 21 to be stored in the blood reservoir 3 exerts an influence on a state of the patient. Accordingly, it is demanded to safely and reliably manage the amount of the blood 21 (position of the blood surface 22) to be stored in the blood reservoir 3.

Here, examples of prior detection methods of a liquid surface include a detection method of an electrostatic capacitance scheme in which the liquid surface is detected on the basis of a change in an electrostatic capacitance that is generated between two electrodes, and a detection method of an ultrasound scheme in which the liquid surface is detected on the basis of the time from when ultrasound is issued to when the ultrasound is returned after being reflected on the liquid. However, the liquid surface detection methods of the electrostatic capacitance scheme and the ultrasound scheme can detect whether the liquid surface is lower than a prescribed liquid surface position, but cannot detect a continuous change in the liquid surface in some cases. Moreover, a liquid surface being lower than a prescribed liquid surface position cannot be detected in some cases, due to the shape of a container in which the liquid is stored, and a surrounding environment.

Moreover, another detection method of a liquid surface includes a detection method in which an image of light having transmitted through a container including a liquid is imaged, and a liquid surface is detected on the basis of the intensity of the light the image of which has been imaged. However, blood has comparatively high viscosity, and thus is easy to adhere on an inner wall of a blood reservoir. Accordingly, even when the position of the blood surface of the blood stored in the blood reservoir is lowered, the blood in the blood reservoir sticks and remains on the inner wall of the blood reservoir in some cases. Accordingly, only imaging the light having transmitted through the container including a liquid by an imaging unit causes a noise to be generated by the blood having adhered on the inner wall of the blood reservoir, and the position of the blood surface of the blood stored in the blood reservoir cannot be reliably detected in some cases.

In contrast, in the extracorporeal circulation apparatus 2 according to the embodiment, control to determine the position of the blood surface 22 is executed on the basis of the presence or absence of consecutiveness between pieces of the presence information acquired along at least one of a first direction parallel to the blood surface 22 of the blood 21 stored in the blood reservoir 3 and a second direction perpendicular to the blood surface 22 of the blood 21 stored in the blood reservoir 3 among pieces of the presence information on the blood 21 transmitted from the imaging unit 9. In other words, the control unit 7 finds the location of blood surface 22 by identifying locations on the wall surface where there is consecutiveness between pieces of the presence information acquired along at least one of the first direction parallel to the blood surface 22 and the second direction perpendicular to the blood surface 22.

The first direction parallel to the blood surface 22 is specifically a horizontal direction. Moreover, the second direction perpendicular to the blood surface 22 is specifically a vertical direction.

With the extracorporeal circulation apparatus 2 according to the embodiment, the control unit 7 can remove a noise that is generated by the blood adhered on the inner wall of the blood reservoir 3. This enables the extracorporeal circulation apparatus 2 according to the embodiment to reliably detect the position of the blood surface 22 of the blood 21 stored in the blood reservoir 3. Hereinafter, the control to determine the position of the blood surface 22 by the control unit 7 will be described in details with reference to the drawings.

Figure 2:
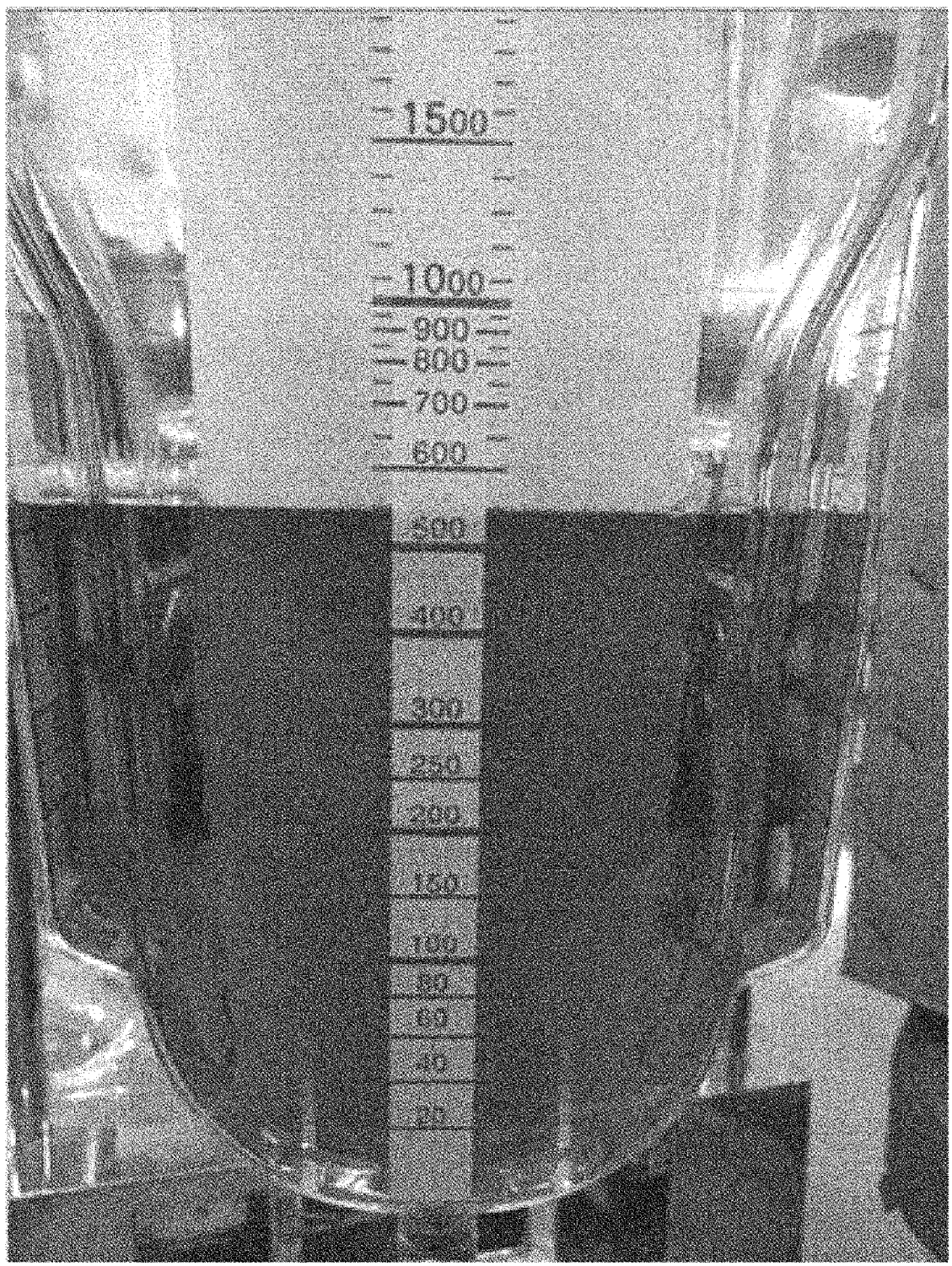
FIG. 2 is a photograph exemplifying one example of an image imaged by an imaging unit according to the embodiment.
Figure 3:
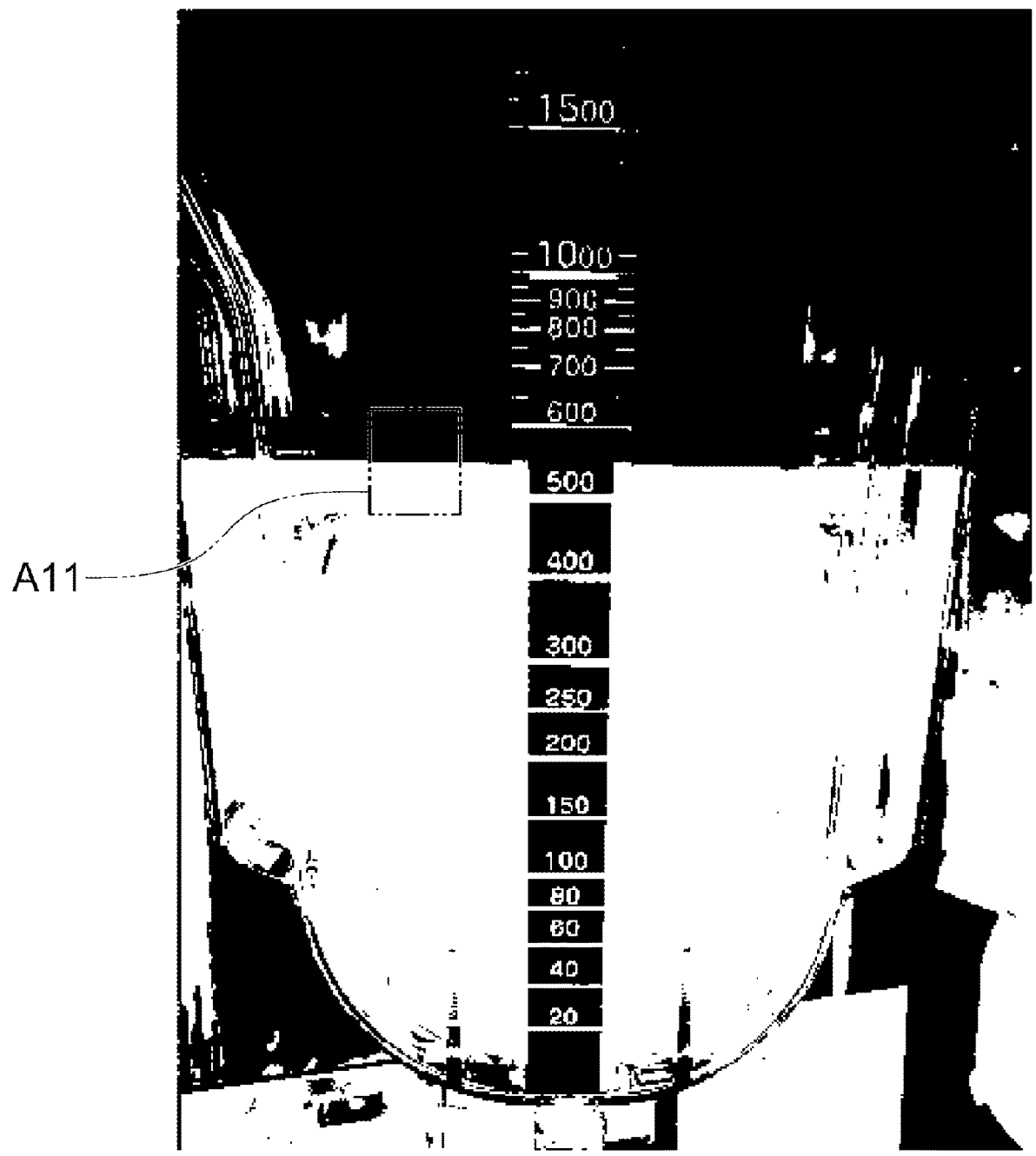
FIG. 3 is a view exemplifying one example of a binary image obtained due to a binarization process executed by a control unit according to the embodiment.

FIG. 2 is a photograph exemplifying one example of an image imaged by the imaging unit according to the embodiment. FIG. 3 is a view exemplifying one example of a binary image obtained due to a binarization process executed by the control unit according to the embodiment. FIG. 4 is a diagram for explaining control to determine the position of a blood surface by the control unit according to the embodiment.

As illustrated in FIG. 2, the imaging unit 9 images the blood surface 22 of the blood 21 stored in the blood reservoir 3. Note that, FIG. 2 illustrates an image (gray-scaled image) when the control unit 7 executes gray-scaling of a color image imaged by the imaging unit 9. Note that, the control unit 7 according to the embodiment may execute a binarization process to a color image imaged by the imaging unit 9, or may execute the gray-scaling of a color image imaged by the imaging unit 9 and execute the binarization process to the gray-scaled image. In the context of image information, binarization sets each pixel within an image to one of two binary values (e.g., representing two colors such as Black and White) based on a threshold. For other types of information, such as temperature measurements described below, binarization likewise comprises collapsing detected values down to two detection values using a threshold. In each case, the threshold is selected to distinguish between locations where blood is present against the reservoir wall and locations where it is not present.

When executing a binarization process to a color image, the control unit 7 extracts a portion in which the brightness (intensity) of each of red (R), green (G), and blue (B) falls within a predetermined range in the color image imaged by the imaging unit 9, and executes the binarization process thereto. For example, when each of red, green, and blue is represented by 256 levels of gray, because the blood includes a component of red, the control unit 7 extracts a portion in which the component of red is included within a range from 0 or more to 255 or less, the component of green is included within a range from 0 or more to 50 or less, the component of blue is included within a range from 0 or more to 50 or less, in a color image imaged by the imaging unit 9, and executes the binarization process thereto. In other words, when the control unit 7 executes the binarization process to the color image, presence information on the blood 21 that is acquired by the imaging unit 9 is color information. Note that, the predetermined range of the brightness (intensity) of each color is not limited only thereto.

When executing a binarization process to a gray-scaled image, the control unit 7 extracts a portion in which the brightness is a threshold (reference brightness) or more, in the gray-scaled image, and executes the binarization process thereto. For example, when a gray-scaled image is represented in 256 levels of gray, the control unit 7 extracts a portion in which the brightness is within the presence information on the blood 21, in the gray-scaled image, and executes the binarization process thereto. In other words, when the control unit 7 executes the binarization process to a gray-scaled image, the presence information on the blood 21 that is acquired by the imaging unit 9 is color information. Note that, the threshold in the binarization process is not limited only thereto.

In the description of the present application, the "color information" includes at least any of the hue, the chroma, and the lightness (i.e., intensity), and includes not only presence information on the blood represented by a color image, but also presence information on the blood represented by a gray-scaled image that is distinguished by the lightness of a white color, the lightness of a gray color, and the lightness of a black color. The control unit 7 executes the binarization process on the basis of the color information transmitted from the imaging unit 9. FIG. 3 illustrates one example of a binary image obtained by the binarization process to the color image or the gray-scaled image. Moreover, FIG. 4(*a*) to FIG. 4(*c*) each illustrate one example of a diagram illustrating an image in a region A11 illustrated in FIG. 3 using pixels.

In the diagrams exemplified in FIG. 4(*a*) to FIG. 4(*c*), when the brightness of each pixel in the image illustrated in FIG. 2 is included within a predetermined range or is a threshold or more, the control unit 7 converts the pixel into "white" (W). On the other hand, when the brightness of each pixel in the image illustrated in FIG. 2 is not included within the predetermined range or is less than the threshold, the control unit 7 converts the pixel into "black" (B). Note that, the converted color by the control unit 7 is not limited only thereto. For example, when the brightness of each pixel in the image illustrated in FIG. 2 falls within a predetermined range or is a threshold or more, the control unit 7 may convert the pixel into "B", or when the brightness of each pixel in the image illustrated in FIG. 2 does not fall within the predetermined range or is less than the threshold, the control unit 7 may convert the pixel into "W". Alternatively, the control unit 7 may convert the pixel into a color other than "W" and "B".

Figure 4A:
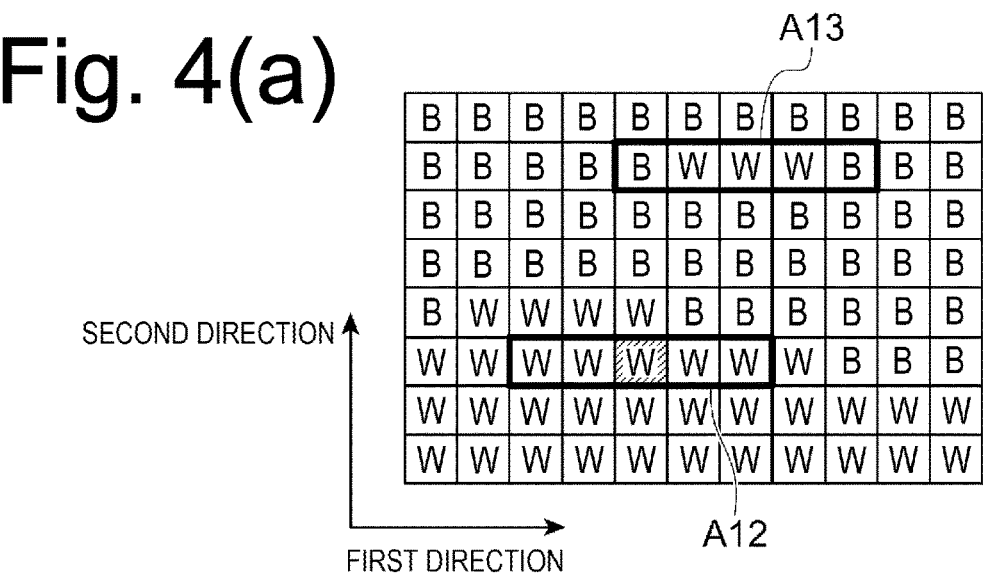
FIGS. 4($a$), 4($b$), and 4($c$) are diagrams for explaining the use of an array of detection values to determine the position of a blood surface by the control unit according to the embodiment.

For example, as a region A12 illustrated in FIG. 4(a), when there are five consecutive pieces of presence information (W) on the blood 21 acquired along the first direction parallel to the blood surface 22, the control unit 7 determines that the blood 21 is present in the center pixel (hatched pixel of "W") among the five pixels. In other words, the center pixel is a candidate for identifying the location of the blood surface. On the other hand, for example, as a region A13 illustrated in FIG. 4(a), there are not five consecutive pieces of the presence information (W) on the blood 21 acquired along the first direction parallel to the blood surface 22, the control unit 7 determines that the blood 21 is not present in the center pixel among the five pixels (i.e., the center pixel is not a candidate for finding the blood surface). In other words, the control unit 7 determines whether the blood 21 is present on the basis of the presence or absence of consecutiveness between pieces of the presence information on the blood 21 acquired along the first direction parallel to the blood surface 22.

Figure 4B:
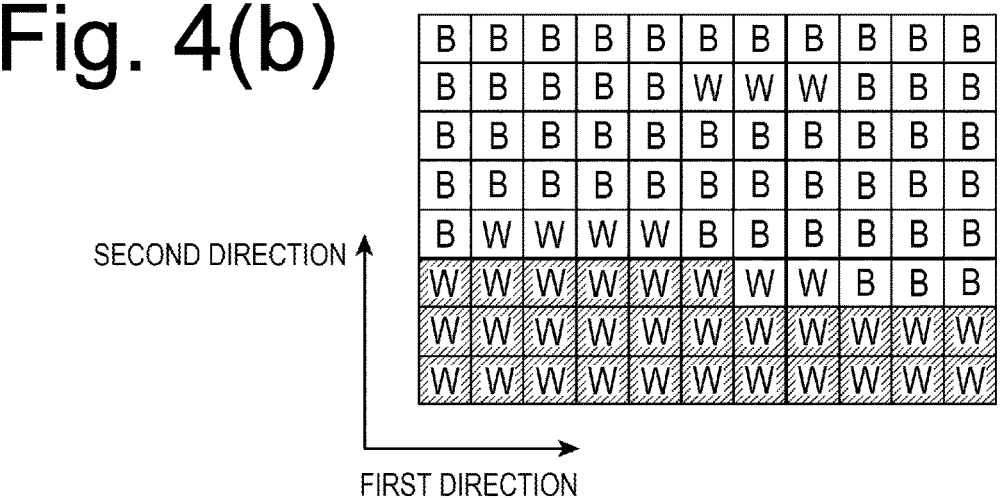

Hatched pixels of "W" illustrated in FIG. 4(b) indicate one example of pixels in which the control unit 7 has determined that the blood 21 is present in this manner, thus identifying pixels which might correspond to the blood surface). Subsequently, the control unit 7 extracts, among the pixels in which the control unit 7 has determined that the blood 21 is present, a pixel in which a position in the second direction (vertical direction) is highest. Hatched pixels of "W" illustrated in FIG. 4(c) indicate one example of pixels in which the control unit 7 has determined that the position in the second direction (vertical direction) is highest. For improving accuracy of the result, an average height of the highest pixel from each vertical row of pixels is preferably determined in order to characterize the location of the blood surface. In other words, among the pixels having been determined as the blood 21 being present, six pixels of "W" are present in the third row from the bottom in the second direction. Moreover, among the pixels having been determined as the blood 21 being present, five pixels of "W" are present in the second row from the bottom in the second direction. Therefore, the control unit 7 determines a value $((3\times6+2\times5)/11\approx2.5)$ obtained by dividing the sum $(3\times6+2\times5)$ of the product $(3\times6)$ of the row number (3) of the third row and the number (6) of "W" pixels in the third row, and the product $(2\times5)$ of the row number (2) of the second row and the number (5) of "W" pixels in the second row, by the total number $(6+5=11)$ of "W" pixels, as the position of the blood surface 22. In other words, in the diagrams exemplified in FIG. 4(a) to FIG. 4(c), the control unit 7 determines that the position of the blood surface 22 of the blood 21 stored in the blood reservoir 3 is present in the approximately 2.5-th row from the bottom in the second direction.

In this manner, the control unit 7 according to the embodiment determines whether the blood 21 is present on the basis of the presence or absence of consecutiveness between pieces of the presence information on the blood 21 acquired along the first direction parallel to the blood surface 22, and determines the position of the blood surface 22. Note that, in the embodiment, the explanation has been made by exemplifying a case where the control unit 7 determines the position of the blood surface 22 on the basis of the presence or absence of consecutiveness between pieces of the presence information on the blood 21 acquired along the first direction parallel to the blood surface 22. Note that, the embodiment is not limited only thereto, but the control unit 7 may determine the position of the blood surface 22 on the basis of the presence or absence of consecutiveness between pieces of the presence information on the blood 21 acquired along the second direction perpendicular to the blood surface 22, or may determine the position of the blood surface 22 on the basis of the presence or absence of consecutiveness between pieces of the presence information on the blood 21 acquired along the first direction and the second direction. Moreover, the predetermined number ("5" in the embodiment) of consecutive pieces of the presence information on the blood 21 is one example, and is not limited thereto. Moreover, a portion ("center" in the embodiment), among a plurality of pixels, of the pixel to be determined as the blood 21 being present by the control unit 7 is one example, and is not limited only thereto. For example, the control unit 7 may determine that the blood 21 is present, among the five pixels, in the center three pixels.

With the extracorporeal circulation apparatus 2 according to the embodiment, the control unit 7 determines whether there is consecutiveness between pieces of the presence information acquired along at least one of the first direction parallel to the blood surface 22 and the second direction perpendicular to the blood surface 22, and determines the position of the blood surface 22 of the blood 21 stored in the blood reservoir 3 on the basis of the determination result. Accordingly, the control unit 7 can remove a noise that is generated by the blood adhered on the inner wall of the blood reservoir 3. This enables the extracorporeal circulation apparatus 2 according to the embodiment to reliably detect the position of the blood surface 22 of the blood 21 stored in the blood reservoir 3.

Moreover, generally, a filter member for removing bubbles and foreign matters in the blood flowing into an inside of the blood reservoir 3, which is not illustrated, is disposed inside the blood reservoir 3. The filter member is formed of porous materials having a property of causing the blood 21 to transmit (pass) therethrough. Examples of porous materials for the filter member include mesh (net)-like raw materials, woven fabric, and nonwoven fabric, or include a material in which these materials are arbitrarily combined (for example, laminated) to one another. Because the filter member has comparatively fine meshes, depending on the amount of blood flowing into the inside of the blood reservoir, the amount of blood passing thorough the filter member may be less than the amount of blood flowing into the blood reservoir in some cases. This may cause the blood surface inside the filter member to be higher than the blood surface (blood surface that is intended to be originally detected) in the blood reservoir in some cases. Accordingly, a noise due to the filter member may be generated in some cases.

In contrast, with the extracorporeal circulation apparatus 2 according to the embodiment, the control unit 7 can determine whether there is consecutiveness between pieces of the presence information acquired along both of the first direction parallel to the blood surface 22 and the second direction perpendicular to the blood surface 22, and can determine the position of the blood surface 22 of the blood 21 stored in the blood reservoir 3 on the basis of the determination result. This enables the extracorporeal circulation apparatus 2 according to the embodiment to detect the position of the blood surface that rises in the filter member and to remove a noise (noise due to the filter member) from the blood surface that rises in the filter member, and thus to reliably detect the position of the blood surface 22 of the blood 21 stored in the blood reservoir 3.

Moreover, in the embodiment, the presence information acquisition unit that acquires presence information on the blood 21 is the imaging unit 9 that images the blood surface. Accordingly, the imaging unit 9 images the blood surface 22 in a noncontact state to the blood 21, and acquires presence information on the blood 21 stored in the blood reservoir 3. This enables the extracorporeal circulation apparatus 2 according to the embodiment to detect a continuous change in the blood surface 22, unlike the liquid surface detection methods of the electrostatic capacitance scheme and of the ultrasound scheme.

Moreover, in the embodiment, the presence information on the blood 21 is color information. The blood contains a component of red. Therefore, the control unit 7 executes a binarization process on the basis of the color information transmitted from the imaging unit 9, extracts the blood 21 containing the component of red, and determines the position of the blood surface 22, and thus can rapidly and reliably determine the position of the blood surface 22.

Moreover, as described in the foregoing related to FIG. 1, the display unit 8 displays, on the basis of an information signal transmitted from the control unit 7, information on the position of the blood surface 22 of the blood 21 stored in the blood reservoir 3. Accordingly, a health care worker can more easily manage the position of the blood surface 22 in the blood reservoir 3 by checking the display unit 8. This enables the extracorporeal circulation apparatus 2 according to the embodiment to attain the enhancement of support with respect to a procedure by the health care worker.

Moreover, the imaging unit 9 is disposed to allow the position of the blood surface 22 to be detected, so that the preparation for using the extracorporeal circulation apparatus 2 becomes easy. Moreover, the extracorporeal circulation apparatus 2 can detect the position of the blood surface 22 without being influenced by the shape of the blood reservoir 3. In other words, a dedicated blood reservoir having a specified shape becomes unnecessary.

In addition, when the position of the blood surface 22 has not been detected, the display unit 8 can display the fact that the position of the blood surface 22 cannot be recognized on the basis of an information signal transmitted from the control unit 7. Moreover, the extracorporeal circulation apparatus 2 can reliably detect the position of the blood surface 22 of the blood 21 stored in the blood reservoir 3, and thus can prevent generation of a state (false negative) in which no warning is informed regardless that the position of the blood surface 22 in the blood reservoir 3 has been lowered from a warning position, for example.

Next, a second embodiment of the present invention will be described. Note that, when components of an extracorporeal circulation apparatus 2A according to the second embodiment are similar to components of the extracorporeal circulation apparatus 2 according to the first embodiment described in the foregoing related to FIG. 1, overlapping explanations are omitted as appropriate, and differences will be mainly described hereinafter.

Figure 5:
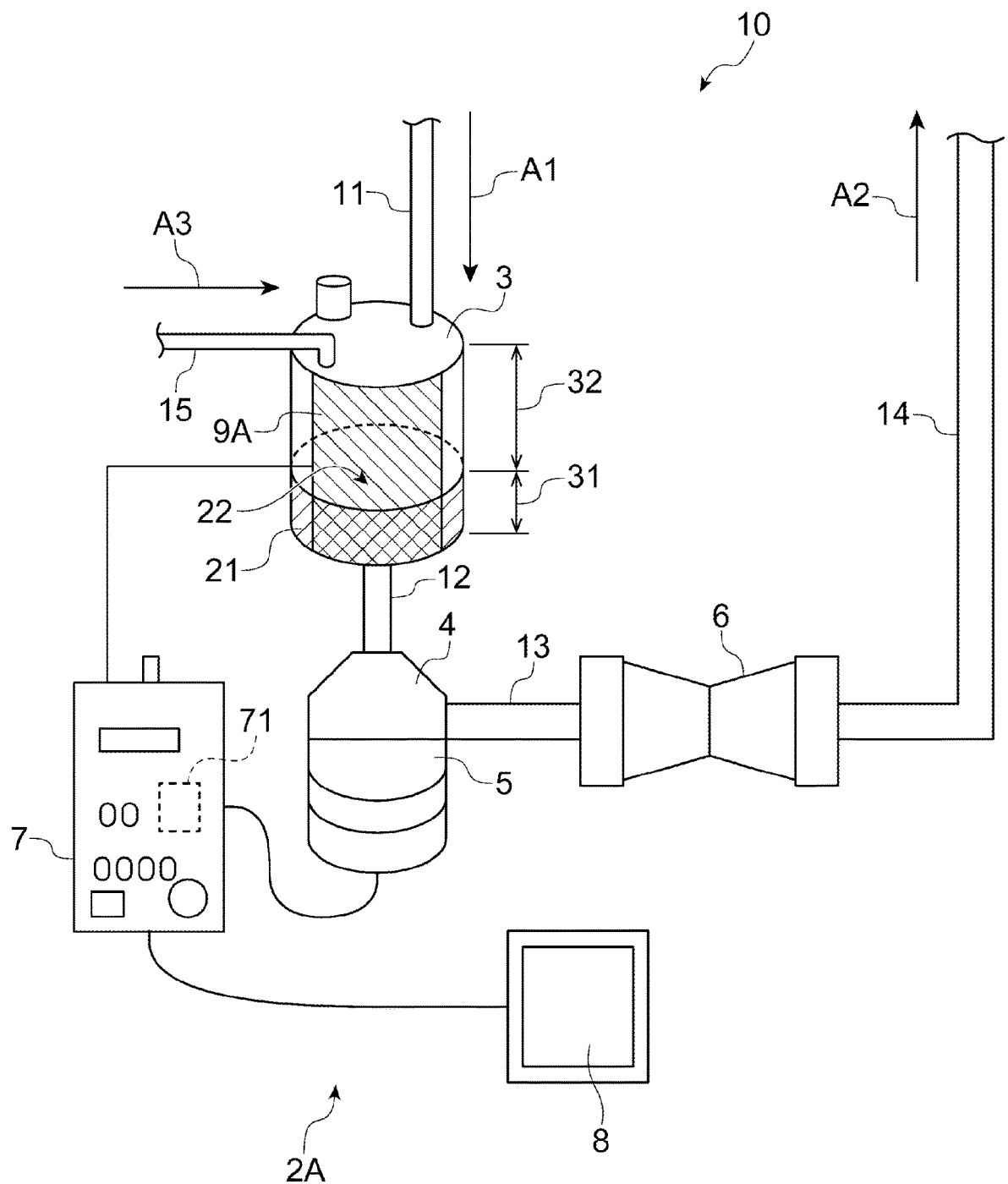
FIG. 5 is a system diagram illustrating an extracorporeal circulation apparatus according to a second embodiment of the present invention.

FIG. 5 is a system diagram illustrating the extracorporeal circulation apparatus according to the second embodiment of the present invention. The extracorporeal circulation apparatus 2A according to the embodiment provided with the blood reservoir 3, the pump 4, the motor 5, the oxygenator 6, the control unit 7, the display unit 8, a temperature detection unit (presence information acquisition unit) 9A, and the circulation circuit 10. In other words, the extracorporeal circulation apparatus 2A according to the embodiment is provided with the temperature detection unit 9A as the presence information acquisition unit, instead of the imaging unit 9 (see FIG. 1). In this regard, the extracorporeal circulation apparatus 2A according to the second embodiment is different from the extracorporeal circulation apparatus 2 according to the first embodiment. The other structure is similar to the structure of the extracorporeal circulation apparatus 2 according to the first embodiment described in the foregoing related to FIG. 1.

The temperature detection unit 9A corresponds to the presence information acquisition unit of the present invention, and acquires presence information on the blood 21 stored in the blood reservoir 3. Specifically, the temperature detection unit 9A is attached to a wall surface of the blood reservoir 3, and detects the temperature of the wall surface of the blood reservoir 3 along at least one of the first direction and the second direction. Temperature information on the wall surface of the blood reservoir 3 detected by the temperature detection unit 9A is transmitted to the control unit 7.

The control unit 7 extracts a portion the temperature of which is a threshold (reference temperature) or higher, in the temperature information on the wall surface of the blood reservoir 3 detected by the temperature detection unit 9A, and executes a binarization process thereto. In other words, the temperature of the blood 21 removed from the patient and stored in the blood reservoir 3 is higher than the temperature of the air. Accordingly, as illustrated in FIG. 5, the temperature of the wall surface of a blood 21-holding portion 31 of the blood reservoir 3 is higher than the temperature of the wall surface of a no blood 21-holding portion (portion of the air) 32 of the blood reservoir 3. The temperature detection unit 9A detects such a difference and a change in the temperature between the wall surfaces of the blood reservoir 3, and acquires presence information on the blood 21 stored in the blood reservoir 3. In other words, the presence information on the blood 21 acquired by the temperature detection unit 9A is temperature information. Further, the control unit 7 executes a binarization process on the basis of the temperature information transmitted from the temperature detection unit 9A.

In the diagrams exemplified in FIG. 4(*a*) to FIG. 4(*c*), when the temperature of a wall surface portion of the blood reservoir 3 detected by the temperature detection unit 9A is a threshold or higher, the control unit 7 converts pixels corresponding to the wall surface portion into "W". On the other hand, when the temperature of the wall surface portion of the blood reservoir 3 detected by the temperature detection unit 9A is lower than a threshold, the control unit 7 converts pixels corresponding to the wall surface portion into "B". Subsequently, the control unit 7 determines the position of the blood surface 22 of the blood 21 stored in the blood reservoir 3, by the determination method described in the foregoing related to FIG. 4(*a*) to FIG. 4(*c*).

With the extracorporeal circulation apparatus 2A according to the embodiment, the presence information acquisition unit that acquires presence information on the blood 21 is the temperature detection unit 9A that detects the temperature of the wall surface of the blood reservoir 3 along at least one of the first direction and the second direction. The temperature detection unit 9A detects a difference and a change in the temperature between the wall surfaces of the blood reservoir 3 along at least one of the first direction and the second direction, and acquires presence information on the blood 21 stored in the blood reservoir 3. This enables the extracorporeal circulation apparatus 2A according to the embodiment to detect a continuous change in the blood surface 22, unlike the liquid surface detection methods of the electrostatic capacitance scheme and of the ultrasound scheme.

Moreover, in the embodiment, the presence information on the blood 21 is temperature information. As described in the foregoing, the temperature of the wall surface of the blood 21-holding portion 31 of the blood reservoir 3 is higher than the temperature of the wall surface of the no blood 21-holding portion 32 of the blood reservoir 3. Therefore, the control unit 7 executes a binarization process on the basis of the temperature information transmitted from the temperature detection unit 9A, extracts a portion in which the blood 21 has been stored in the blood reservoir 3, and determines the position of the blood surface 22, and thus can more rapidly and reliably determine the position of the blood surface 22. Moreover, the effect similar to the effect described in the foregoing related to the extracorporeal circulation apparatus 2 according to the first embodiment can be obtained.

Next, a third embodiment of the present invention will be described. Note that, when components of an extracorporeal circulation apparatus 2B according to the third embodiment are similar to components of the extracorporeal circulation apparatus 2 according to the first embodiment described in the foregoing related to FIG. 1 and components of the extracorporeal circulation apparatus 2A according to the second embodiment described in the foregoing related to FIG. 5, overlapping explanations are omitted as appropriate, and differences will be mainly described hereinafter.

Figure 6:
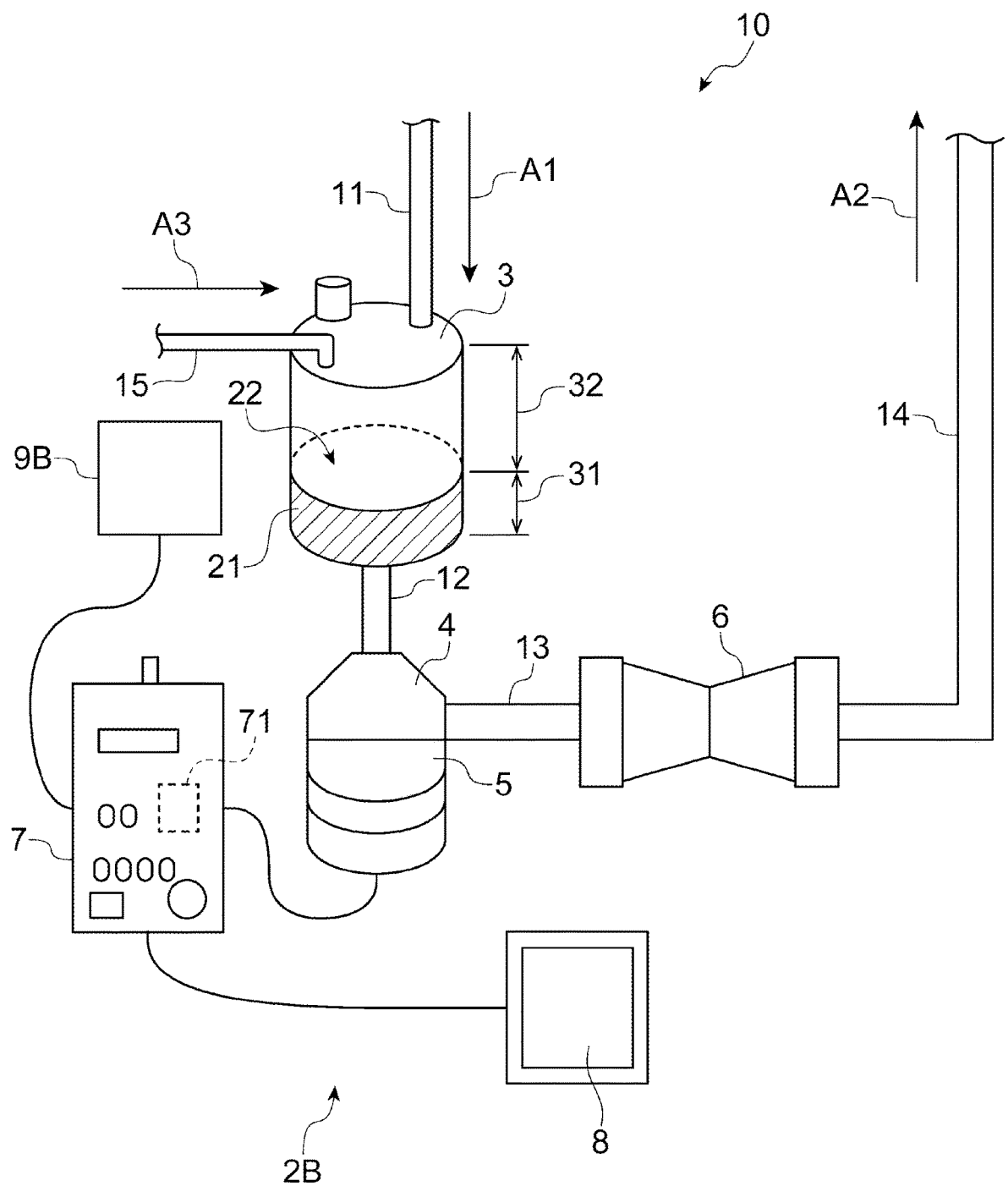
FIG. 6 is a system diagram illustrating an extracorporeal circulation apparatus according to a third embodiment of the present invention.

FIG. 6 is a system diagram illustrating the extracorporeal circulation apparatus according to the third embodiment of the present invention. The extracorporeal circulation apparatus 2B according to the embodiment is provided with the blood reservoir 3, the pump 4, the motor 5, the oxygenator 6, the control unit 7, the display unit 8, a thermography unit (presence information acquisition unit) 9B, and the circulation circuit 10. In other words, the extracorporeal circulation apparatus 2B according to the embodiment is provided with the thermography unit 9B as the presence information acquisition unit, instead of the imaging unit 9 (see FIG. 1). Moreover, the extracorporeal circulation apparatus 2B according to the embodiment is provided with the thermography unit 9B as the presence information acquisition unit, instead of the temperature detection unit 9A (see FIG. 5). In this regard, the extracorporeal circulation apparatus 2B according to the third embodiment is different from the extracorporeal circulation apparatus 2 according to the first embodiment and the extracorporeal circulation apparatus 2A according to the second embodiment. The other structure is similar to the structures of the extracorporeal circulation apparatus 2 according to the first embodiment described in the foregoing related to FIG. 1 and the extracorporeal circulation apparatus 2A according to the second embodiment described in the foregoing related to FIG. 5.

The thermography unit 9B corresponds to the presence information acquisition unit of the present invention, and acquires presence information on the blood 21 stored in the blood reservoir 3. Specifically, the thermography unit 9B is disposed outside the blood reservoir 3, and detects infrared rays emitted from the blood reservoir 3 in which the blood 21 has been stored. The radiation amount of infrared rays detected by the thermography unit 9B is transmitted to the control unit 7.

The control unit 7 extracts a portion the radiation amount of which is a threshold (reference radiation amount) or more in the radiation amount of infrared rays detected by the thermography 9B unit, and executes a binarization process thereto. Alternatively, the amount of infrared rays emitted from a measurement object depends on the temperature of the measurement object. Accordingly, the presence information (radiation amount of infrared rays) transmitted from the thermography unit 9B is equivalent to the temperature information. Accordingly, the control unit 7 may converts the radiation amount of infrared rays detected by the thermography unit 9B into the temperature information in the blood reservoir 3 in which the blood 21 has been stored. In this case, the control unit 7 extracts a portion the temperature of which is a threshold (reference temperature) or higher, in the temperature information on the blood reservoir, and executes a binarization process thereto.

As described in the foregoing related to FIG. 5, the temperature of the blood 21 removed from the patient and stored in the blood reservoir 3 is higher than the temperature of the air. Accordingly, the temperature of the portion 31 in which the blood 21 has been stored in the blood reservoir 3 is higher than the temperature of the portion (portion of the air) 32 in which the blood 21 has not been stored in the blood reservoir 3. The thermography unit 9B detects such a difference and a change in the temperature of the blood reservoir 3 as a difference and a change in the amount of infrared rays emitted from the blood reservoir 3, and acquires presence information on the blood 21 stored in the blood reservoir 3. In other words, the presence information on the blood 21 acquired by the thermography unit 9B corresponds to the temperature information. Further, the control unit 7 executes a binarization process on the basis of the temperature information transmitted from the thermography unit 9B.

Figure 4C:
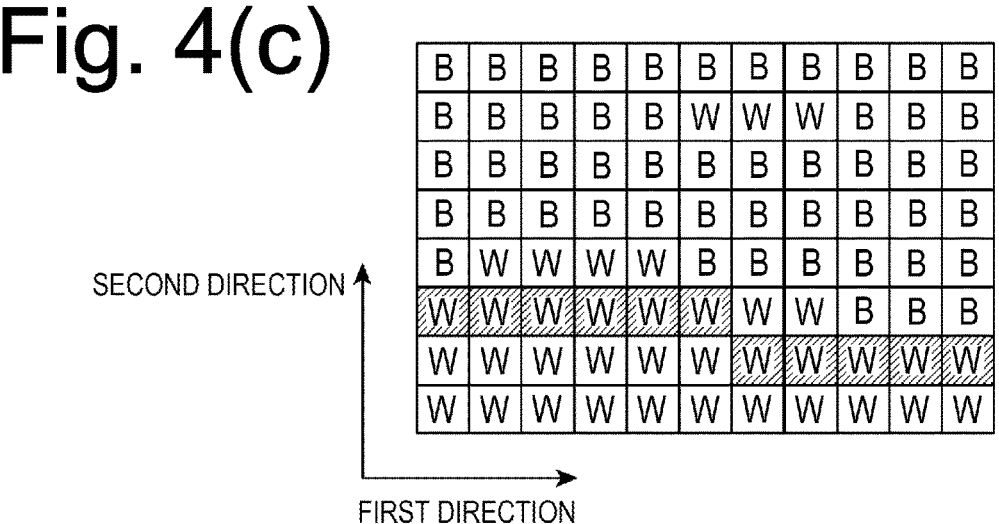

In the diagrams exemplified in FIG. 4(a) to FIG. 4(c), when the temperature of a portion of the blood reservoir 3 detected by the thermography unit 9B is a threshold or higher, the control unit 7 converts pixels corresponding to the portion into "W". On the other hand, when the temperature of a portion of the blood reservoir 3 detected by the thermography unit 9B is lower than a threshold, the control unit 7 converts pixels corresponding to the wall surface portion into "B". Subsequently, the control unit 7 determines the position of the blood surface 22 of the blood 21 stored in the blood reservoir 3, by the determination method described in the foregoing related to FIG. 4(a) to FIG. 4(c).

With the extracorporeal circulation apparatus 2B according to the embodiment, the presence information acquisition unit that acquires presence information on the blood 21 is the thermography unit 9B that detects infrared rays emitted from the blood reservoir 3 in which the blood 21 has been stored. As described in the foregoing, the thermography unit 9B detects a difference and a change in the temperature of the blood reservoir 3 as a difference and a change in the amount of infrared rays emitted from the blood reservoir 3, and acquires presence information on the blood 21 stored in the blood reservoir 3. This enables the extracorporeal circulation apparatus 2B according to the embodiment to detect a continuous change in the blood surface 22, unlike the liquid surface detection methods of the electrostatic capacitance scheme and of the ultrasound scheme. Moreover, the effect similar to the effects described in the foregoing related to the extracorporeal circulation apparatus 2 according to the first embodiment and the extracorporeal circulation apparatus 2A according to the second embodiment can be obtained.

Next, another control executed by the control unit 7 according to the embodiment will be described. The control that will be described below is executable in the control units 7 of the extracorporeal circulation apparatuses 2, 2A, and 2B according to the first to the third embodiments.

Figure 7:
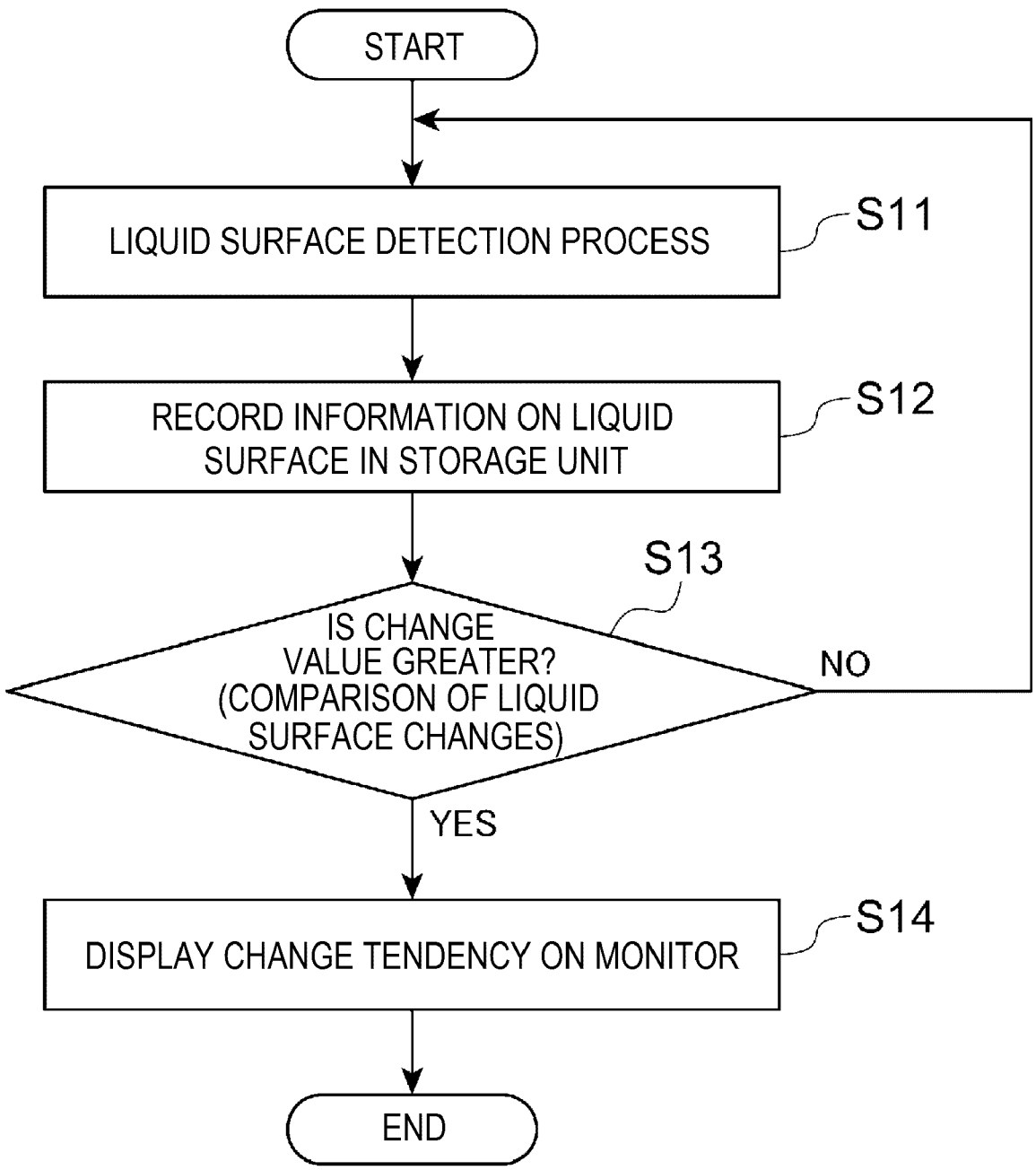
FIG. 7 is a flowchart for explaining change tendency notification control according to the embodiments.

FIG. 7 is a flowchart for explaining change tendency notification control according to the embodiments. Firstly, at Step S11, the control unit 7 detects the position of the blood surface 22 of the blood 21 stored in the blood reservoir 3 (liquid surface detection process). Moreover, the control unit 7 has a timer function and a time switch function, and can acquire time information, for example, a time of day, at Step S11. The process in the determination method described in the foregoing related to FIG. 4(a) to FIG. 4(c), FIG. 5, and FIG. 6 is applied to the liquid surface detection process at Step S11. Subsequently, at Step S12, the control unit 7 stores (holds) information on the position of the blood surface 22 and time information, in the storage unit 71. Subsequently, at Step S13, the control unit 7 determines whether a change value between information on the position of the blood surface 22 (past position of the blood surface 22) stored in the storage unit 71 and information on the position of the blood surface 22 (current position of the blood surface 22) newly determined at Step S11 is greater than a predetermined change value. For example, the change value between information on the position of the blood surface 22 stored in the storage unit 71 and information on the position of the blood surface 22 determined at Step S11 is a difference value between the position of the blood surface 22 stored in the storage unit 71 and the position of the blood surface 22 determined at Step S11.

If the change value between information on the position of the blood surface 22 stored in the storage unit 71 and information on the position of the blood surface 22 determined at Step S11 is greater than the predetermined change value (Step S13: YES), at Step S14, the control unit 7 transmits an information signal to the display unit 8, and makes a notification about a change tendency of the position of the blood surface 22 by the display unit 8. On the other hand, if the change value between information on the position of the blood surface 22 stored in the storage unit 71 and information on the position of the blood surface 22 determined at Step S11 is not greater than the predetermined change value (Step S13: NO), at Step S11, the control unit 7 detects again the position of the blood surface 22 of the blood 21 stored in the blood reservoir 3 (liquid surface detection process).

With the change tendency notification control in the embodiments, before the position of the blood surface 22 in the blood reservoir 3 is lowered than a predetermined position, for example, a warning position, or before approaches the predetermined position, the control unit 7 can notify a health care worker of the change value of the blood surface 22 being greater than the predetermined change value. This enables the extracorporeal circulation apparatuses 2, 2A, and 2B according to the embodiments to attain the enhancement of support with respect to a procedure by the health care worker. Note that, a notification device of a change tendency for the position of the blood surface 22 is not limited to the display unit 8. For example, as a notification device of a change tendency for the position of the blood surface 22, a device that generates a sound may be used. Alternatively, as a notification device of a change tendency for the position of the blood surface 22, a device that emits light, other than the display unit 8, may be used.

Figure 8:
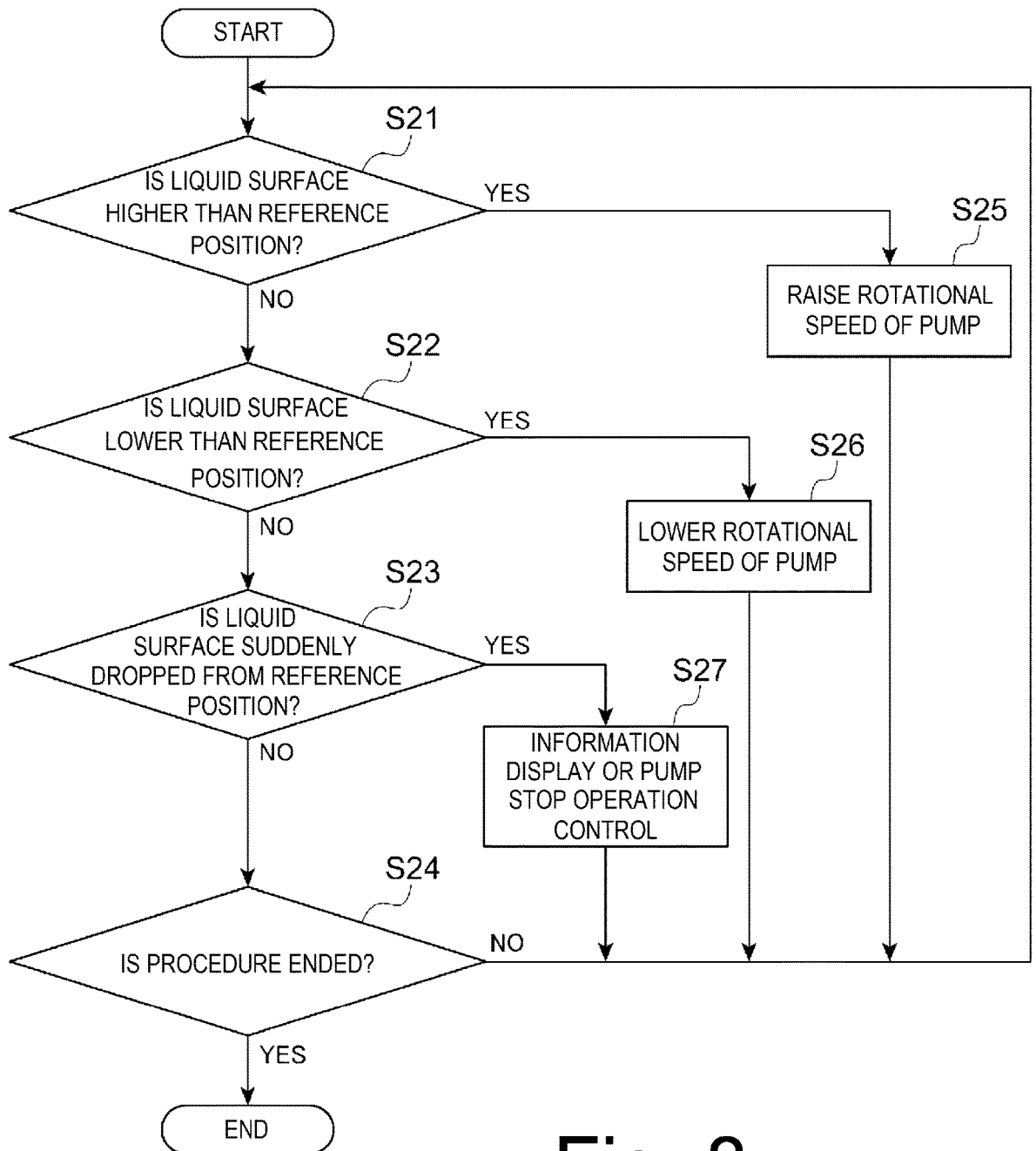
FIG. 8 is a flowchart for explaining liquid surface maintenance control according to the embodiments.

FIG. 8 is a flowchart for explaining liquid surface maintenance control according to the embodiments. Firstly, at Step S21, the control unit 7 determines whether the determined position of the blood surface 22 is higher than a reference position. The "reference position" is the position of the surface 22 of the blood 21 stored in the blood reservoir 3, which may be any desired maximum position to be maintained. If the determined position of the blood surface 22 is higher than the reference position (Step S21: YES), at Step S25, the control unit 7 executes control to raise the rotational speed of the motor 5, and raises the rotational speed of the pump 4. This increases the amount of blood to be sent out from the pump 4. Accordingly, the amount of blood to be sent from the blood reservoir 3 to a patient increases, thereby decreasing the amount of blood in the blood reservoir 3. At Step S21 subsequent to Step S25, the control unit 7 determines again whether the determined position of the blood surface 22 is higher than the reference position.

On the other hand, if the determined position of the blood surface 22 is not higher than the reference position (Step S21: NO), at Step S22, the control unit 7 determines whether the determined position of the blood surface 22 is lower than a reference position (e.g., any desired minimum position to be maintained). If the determined position of the blood surface 22 is lower than the reference position (Step S22: YES), at Step S26, the control unit 7 executes control to lower the rotational speed of the motor 5, and lowers the rotational speed of the pump 4. This decreases the amount of blood to be sent out from the pump 4. Accordingly, the amount of blood to be sent from the blood reservoir 3 to a patient decreases, thereby increasing the amount of blood in the blood reservoir 3. At Step S21 subsequent to Step S26, the control unit 7 determines again whether the determined position of the blood surface 22 is higher than the reference position.

On the other hand, if the determined position of the blood surface 22 is not lower than the minimum reference position (Step S22: NO), at Step S23, the control unit 7 determines whether the determined position of the blood surface 22 has suddenly dropped from a reference position (i.e., a previous position). For example, at Step S23, the control unit 7 determines whether a change speed (change rate) of the determined position (height) of the blood surface 22 is higher than a prescribed change speed (change rate). If the determined position of the blood surface 22 has suddenly dropped from the reference position (Step S23: YES), at Step S27, the control unit 7 executes control to display a change tendency for the position of the blood surface 22 on the display unit 8. Alternatively, at Step S27, the control unit 7 executes control to stop an operation of the pump 4. Alternatively, at Step S27, the control unit 7 executes both of the control to display a change tendency for the position of the blood surface 22 on the display unit 8, and the control to stop the operation of the pump 4. At Step S21 subsequent to Step S27, the control unit 7 determines again whether the determined position of the blood surface 22 is higher than the reference position.

On the other hand, if the determined position of the blood surface 22 has not suddenly dropped from the reference position (Step S23: NO), at Step S24, the control unit 7 determines whether a procedure by a health care worker who uses the extracorporeal circulation apparatus 2, 2A, or 2B is ended. If a procedure by a health care worker who uses the extracorporeal circulation apparatus 2, 2A, or 2B is ended (Step S24: YES), the control unit 7 ends the liquid surface maintenance control. On the other hand, if a procedure by a health care worker who uses the extracorporeal circulation apparatus 2, 2A, or 2B is not ended (Step S24: NO), at Step S21, the control unit 7 determines again whether the determined position of the blood surface 22 is higher than the reference position.

With the liquid surface maintenance control according to the embodiments, when the determined position of the blood surface 22 is higher than the reference position, the control unit 7 executes the control to raise the rotational speed of the pump 4, and when the determined position of the blood surface 22 is lower than the reference position, the control unit 7 executes the control to lower the rotational speed of the pump 4. This maintains the position of the blood surface 22 in the blood reservoir 3 to a constant position (reference position). In other words, the extracorporeal circulation apparatuses 2, 2A, and 2B according to the embodiments can control the position of the blood surface 22 in the blood reservoir 3 to the constant position (reference position). This enables the extracorporeal circulation apparatuses 2, 2A, and 2B according to the embodiments to attain the enhancement of support with respect to a procedure by the healthcare worker.

In the foregoing, the embodiments of the present invention have been described. However, the present invention is not limited to the abovementioned embodiments, but various changes can be made within a range without deviating the scope of the present disclosure. The configurations of the abovementioned embodiments can be partially omitted, or can be arbitrarily combined so as to be different from the above.

What is claimed is:

1. An extracorporeal circulation apparatus that subjects blood to extracorporeal circulation, the extracorporeal circulation apparatus comprising:
    a blood reservoir configured to store the blood temporarily;
    an acquisition unit configured to acquire a plurality of blood detection values spanning a two-dimensional array mapped to a predetermined wall of the reservoir, each blood detection value for a respective element of the array being indicative of whether blood stored in the blood reservoir is detected at a respective wall location; and
    a control unit programmed to determine a position of a surface of the stored blood on the basis of finding a predetermined number of consecutive horizontal elements having a blood detection value indicating a presence of stored blood along a horizontal direction parallel to the surface of the blood stored in the blood reservoir and finding a vertical height of the consecutive horizontal elements in a vertical direction perpendicular to the surface of the blood which is a highest position of consecutive vertical elements having the blood detection value indicating a presence of stored blood which also includes the consecutive horizontal elements;
    wherein the acquisition unit is comprised of an imaging unit that is disposed outside the blood reservoir and captures an image of the blood surface and the wall of the reservoir, and wherein each element of the array is comprised of a respective pixel of the image;
    wherein the imaging unit captures at least one of intensity information and color information; and
    wherein the control unit is configured to execute a binarization process on at least one of the color information or the intensity information to generate the blood detection values.

2. The extracorporeal circulation apparatus according to claim 1 wherein the position of the surface for each row of vertical elements in the vertical direction is determined according to a highest element which is a center element within a predetermined number of consecutive horizontal elements having the blood detection value indicating a presence of stored blood along the horizontal direction.

3. The extracorporeal circulation apparatus according to claim 2 wherein the control unit is configured to determine an average of the heights of the position of the blood surface determined for each row of elements in the vertical direction.

4. The extracorporeal circulation apparatus according to claim 1, further comprising a display unit configured to display information on the position of the blood surface determined by the control unit, the information being transmitted from the control unit.

5. The extracorporeal circulation apparatus according to claim 1, wherein the control unit is configured to include a storage unit configured to store therein the information on the position of the blood surface, and when a change value between stored information on the position of the blood surface in the storage unit and newly determined information on the position of the blood surface is greater than a predetermined change value, then the control unit generates a notification about a change tendency.

6. The extracorporeal circulation apparatus according to claim 1, further comprising:
    a circulation circuit configured to cause the blood to circulate;
    a pump configured to be disposed in the circulation circuit to pump the blood through the circulation circuit; and
    a motor configured to drive the pump on the basis of a signal transmitted from the control unit;
    wherein the control unit is configured to raise a rotational speed of the motor when the determined position of the blood surface is higher than a reference position, and to lower the rotational speed of the motor when the determined position of the blood surface is lower than the reference position.

* * * * *